(12) United States Patent
Pellecchia et al.

(10) Patent No.: US 7,951,832 B2
(45) Date of Patent: May 31, 2011

(54) PYRAZOLE DERIVATIVES AS KINASE INHIBITORS

(75) Inventors: Maurizio Pellecchia, La Jolla, CA (US); Surya De, San Diego, CA (US); Elisa Barile, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 134 days.

(21) Appl. No.: 12/261,584

(22) Filed: Oct. 30, 2008

(65) Prior Publication Data

US 2009/0124621 A1    May 14, 2009

Related U.S. Application Data

(60) Provisional application No. 60/984,302, filed on Oct. 31, 2007.

(51) Int. Cl.
*A61K 31/415* (2006.01)
(52) U.S. Cl. ...................... 514/406; 548/361.1
(58) Field of Classification Search ............... 548/361.1; 514/406
See application file for complete search history.

(56) References Cited

U.S. PATENT DOCUMENTS

| 3,187,006 A | 6/1965 | Druey et al. |
| 4,659,775 A | 4/1987 | Pfenninger et al. |
| 4,938,949 A | 7/1990 | Borch et al. |
| 6,713,474 B2 | 3/2004 | Hirst et al. |
| 6,806,274 B1 | 10/2004 | Crawley et al. |
| 7,071,199 B1 | 7/2006 | Hirst et al. |

FOREIGN PATENT DOCUMENTS

| WO | WO 2003/024931 | * | 9/2002 |
| WO | WO 2007/058626 | * | 5/2007 |
| WO | WO 2007/114926 A2 | | 10/2007 |
| WO | WO 2007/114926 A3 | | 10/2007 |

* cited by examiner

*Primary Examiner* — Yong Chu
*Assistant Examiner* — Valerie Rodriguez-Garcia
(74) *Attorney, Agent, or Firm* — DLA Piper LLP (US)

(57) ABSTRACT

The present invention provides compounds having the general structure I, or a pharmaceutically acceptable salt thereof:

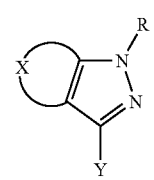

I wherein X is a six-member ring selected from phenyl, pyridine, or pyrimidine; Y is H, an alkenyl, a substituted alkenyl, or alkynyl, and R is H or alkyl. Pharmaceutical compositions for treating various disorders such as cancers, the compositions including compound I are also provided.

6 Claims, 4 Drawing Sheets

PYRAZOLE DERIVATIVES AS KINASE INHIBITORS

CROSS-REFERENCE TO RELATED APPLICATIONS

This application claims priority under 35 U.S.C. §119(e) to U.S. patent application Ser. No. 60/984,302 filed Oct. 31, 2007, the contents of which is herein incorporated by reference in its entirety.

BACKGROUND

1. Field of the Invention

The invention relates generally to compounds useful for the inhibition of kinases, and more specifically, to new pyrazole derivatives, including those comprising pyridine or pyrimidine moieties, that are useful as kinase inhibitors.

2. Background Information

Inhibiting kinases, such as PI3K and mTOR, is one method of treating various diseases, disorders and pathologies. Previously, some compounds that can be useful as inhibitors of certain kinases have been identified and synthesized. However, no compounds have been reported that are capable of targeting and inhibiting kinases PI3 K-AKT-mTOR signaling pathway.

SUMMARY

Currently, there is a need for novel, potent, and selective agents for the treatment of various diseases, disorders and pathologies, such as tumors, as well as for the pharmaceutical compositions including such agents. Such agents can be based on inhibitors of kinases PI3 K-AKT-mTOR signaling pathway.

According to embodiments of the present invention, there are provided compounds having the general structure I, or pharmaceutically acceptable salts thereof:

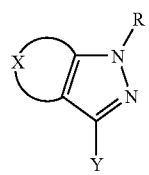

I wherein X is a six-member ring selected from the group consisting of an unsubstituted phenyl, a substituted phenyl, an unsubstituted pyridine, a substituted pyridine, an unsubstituted pyrimidine and a substituted pyrimidine; Y is selected from the group consisting of H, an unsubstituted alkenyl, a substituted alkenyl, an unsubstituted alkynyl and a substituted alkynyl; and R is selected from the group consisting of H, an unsubstituted alkyl and a substituted alkyl.

According to one embodiment of the present invention, compounds are provided having the general structure II:

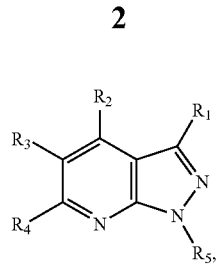

II wherein $R_1$ is selected from a group consisting of a substituted alkenyl and a substituted alkynyl, wherein the substituent(s) in each of the substituted alkenyl and the substituted alkynyl is (are) selected from the group consisting of an aryl, a substituted aryl, a heteroaryl, and a substituted heteroaryl; $R_2$ is selected from a group consisting of a halogen, an unsubstituted aryl, a substituted aryl, an unsubstituted heteroaryl, a substituted heteroaryl, an unsubstituted alkyl, a substituted alkyl, and $(CH_2)_n OR_6$; $R_3$ is selected from a group consisting of H, an unsubstituted aryl, a substituted aryl, an unsubstituted heteroaryl, a substituted heteroaryl, an unsubstituted alkyl, and a substituted alkyl; $R_4$ is selected from a group consisting of OH and $OR_7$; each of $R_5$, $R_6$ and $R_7$ is independently selected from a group consisting of an unsubstituted alkyl and a substituted alkyl; and n is an integer having the value of 1, 2, or 3.

According to embodiments of the present invention, compounds are provided having the general structure IIIA or IIIB:

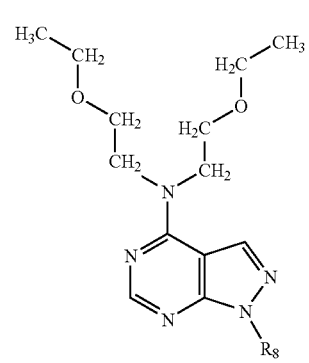

IIIA

IIIB

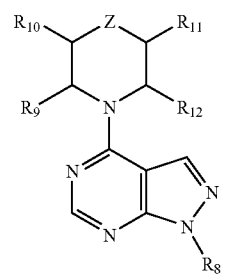

wherein $R_8$ is selected from a group consisting of an unsubstituted aryl and a substituted aryl; each of $R_9$, $R_{10}$, $R_{11}$, and $R_{12}$ is selected from a group consisting of an unsubstituted alkyl, a substituted alkyl, an acyl, an unsubstituted aryl, a substituted aryl, and a halogen; and Z is selected from a group consisting of C, O, and N.

According to other embodiments of the present invention, pharmaceutical compositions are provided for the treatment of various disorders, diseases, and pathologies, such as cancer, the compositions comprising a compound having the general structure II, IIIA or IIIB, and a pharmaceutically acceptable carrier.

According to other embodiments of the present invention, methods for the treatment of various disorders, diseases, and pathologies, such as cancer, are provided, the methods comprising administering to a subject in need thereof a pharmacologically effective dose of a pharmaceutical composition comprising a compound having the general structure II, IIIA or IIIB.

DETAILED DESCRIPTION

Figure 1:
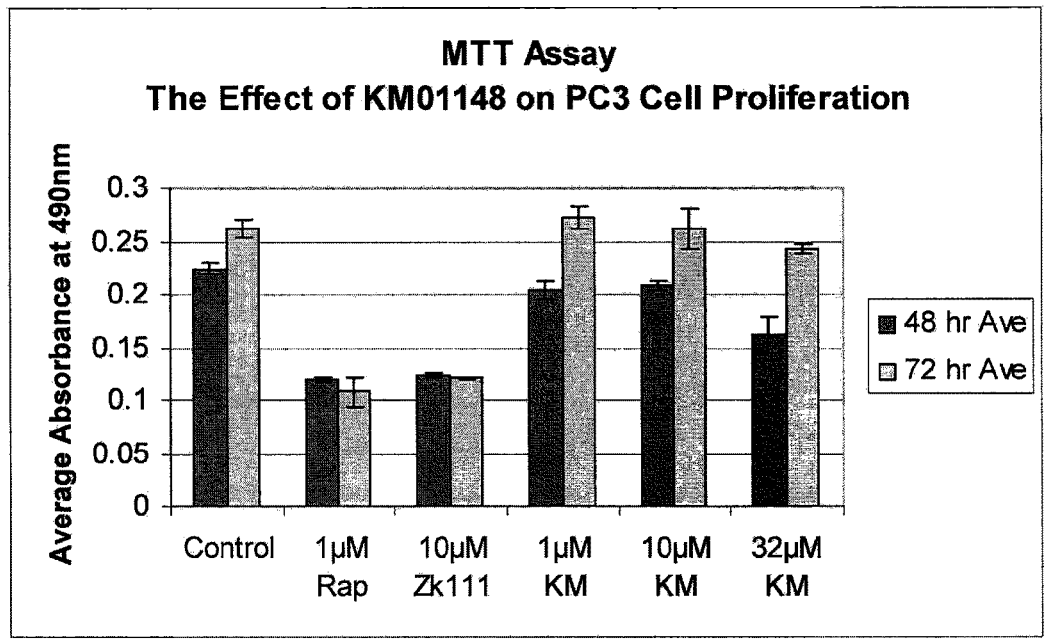
FIG. 1 shows the data on inhibition of PC3 cell proliferation by some compounds of the present invention, according to one embodiment of the present invention.

The following definitions are used, unless otherwise described.

The terms "alkyl" and "substituted alkyl" refer to substituted and unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from a group consisting of halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C$_{1-10}$alkylthio, arylC$_{0-10}$alkylthio, C$_{1-10}$alkylamino, arylC$_{0-10}$alkylamino, N-aryl-N—C$_{0-10}$alkylamino, C$_{1-10}$alkylcarbonyl, arylC$_{0-10}$alkylcarbonyl, C$_{1-10}$alkylcarboxy, arylC$_{0-10}$alkylcarboxy, C$_{1-10}$alkylcarbonylamino, arylC$_{0-10}$alkylcarbonylamino, tetrahydrofuryl, morpholinyl, piperazinyl, hydroxypyronyl, —C$_{0-10}$alkylCOOR$_a$, and —C$_{0-10}$alkylCONR$_b$R$_c$, wherein R$_a$, R$_b$ and R$_c$ are independently selected from hydrogen, alkyl, aryl, or R$_b$ and R$_c$ are taken together with the nitrogen to which they are attached forming a saturated cyclic or unsaturated cyclic system containing 3 to 8 carbon atoms, with at least one substituent.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substitutents described above. The term "alkynyl" refers to straight-chained or branched hydrocarbyl groups having at least one carbon-carbon triple bond, and having between about 2 and about 12 carbon atoms, and the term "substituted alkynyl" refers to alkynyl groups further bearing one or more substitutents described above.

The term "aryl" refers to an unsubstituted, monosubstituted, disubstituted or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from a group consisting of halogen, —OH, —SH, —CN, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N—C$_{0-10}$alkylaminoC$_{0-10}$alkyl, C$_{1-10}$alkylcarbonylC$_{0-10}$alkyl, arylC$_{0-10}$alkylcarbonylC$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, arylC$_{0-10}$alkylcarbonylaminoC$_{0-10}$alkyl, —C$_{0-10}$alkylCOOR$_a$, and —C$_{0-10}$alkylCONR$_b$R$_c$, wherein R$_a$, R$_b$ and R$_c$ are independently selected from hydrogen, alkyl, aryl or R$_b$ and R$_c$ are taken together with the nitrogen to which they are attached forming a saturated cyclic or unsaturated cyclic system containing 3 to 8 carbon atoms with at least one substituent.

The definition of "aryl" includes, but is not limited to, such specific groups as phenyl, biphenyl, naphthyl, dihydronaphthyl, tetrahydronaphthyl, indenyl, indanyl, azulenyl, anthryl, phenanthryl, fluorenyl, pyrenyl and the like.

The terms "heteroaryl", "heterocycle" or "heterocyclic" refer to a monovalent unsaturated group having a single ring or multiple condensed (also known as "fused") rings, from 1 to 8 carbon atoms and from 1 to 4 hetero atoms selected from nitrogen, sulfur or oxygen within the ring. The heteroaryl groups in this invention can be optionally substituted with 1 to 3 substituents selected from a group consisting of: halogen, —H, —SH, —CN, —NO$_2$, trihalomethyl, hydroxypyronyl, C$_{1-10}$alkyl, arylC$_{0-10}$alkyl, C$_{0-10}$alkyloxyC$_{0-10}$alkyl, arylC$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N—C$_{0-10}$alkylaminoC$_{0-10}$alkyl, C$_{1-10}$alkylcarbonylC$_{0-10}$alkyl, arylC$_{0-10}$alkylcarbonylC$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, arylC$_{0-10}$alkylcarbonylaminoC$_{0-10}$alkyl, —C$_{0-10}$alkylCOOR$_a$, and —C$_{0-10}$alkylCONR$_b$R$_c$ wherein R$_a$, R$_b$ and R$_c$ are independently selected from hydrogen, alkyl, aryl, or R$_b$ and R$_c$ are taken together with the nitrogen to which they are attached forming a saturated cyclic or unsaturated cyclic system containing 3 to 8 carbon atoms with at least one substituent.

The definition of "heteroaryl" includes, but is not limited to, such specific groups as thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione and the like.

The term "acyl" refers to a radical —R—C(=O)—, i.e., to a radical derived from an organic acid by the removal of the carboxylic hydroxyl group. Typical examples of acyl groups include acetyl and benzoyl moieties.

The terms "halogen", "halide" or "halo" refer to fluorine, chlorine, bromine, and iodine.

The term "kinase" refers to any enzyme that catalyzes the addition of phosphate groups to a protein residue; for example, serine and threonine kinases catalyze the addition of phosphate groups to serine and threonine residues.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

As used herein, the term "patient" refers to organisms to be treated by the methods of the present invention. Such organisms include, but are not limited to, humans. In the context of the invention, the term "subject" generally refers to an individual who will receive or who has received treatment for the treatment of a disease, disorder or pathology.

According to embodiments of the present invention, there are provided compounds having the general structure I, or pharmaceutically acceptable salts thereof:

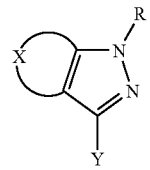

I

In the general structure I, X is a six-member ring selected from the group consisting of an unsubstituted phenyl, a substituted phenyl, an unsubstituted pyridine, a substituted pyridine, an unsubstituted pyrimidine and a substituted pyrimidine; Y is selected from the group consisting of H, an unsubstituted alkenyl, a substituted alkenyl, an unsubstituted alkynyl and a substituted alkynyl; and R is selected from the group consisting of H, an unsubstituted alkyl and a substituted alkyl.

In some embodiments, the compounds of the general structure I may be derivatives of indazole, which are described in more detail below. For these embodiments, accordingly, in the general structure I, X may be an unsubstituted or substituted phenyl having at least one substituent independently selected from the group consisting of an amino group, a substituted amido group, nitro group, an ester group, carboxyl group, and morpholino group.

In other embodiments, the compounds of the general structure I may be derivatives of pyrazolopyridine, which are described in more detail below. For these embodiments, accordingly, in the general structure I, X may be an unsubstituted or substituted pyridine. In yet other embodiments, the compounds of the general structure I may be derivatives of pyrazolopyrimidine, which are described in more detail below. For these embodiments, accordingly, in the general structure I, X may be a substituted pyrimidine having at least one substitutent independently selected from the group consisting of a substituted amino group, morpholino group, piperazino group, and piperidino group.

Examples of some sub-genera that are within the purview of the present invention and are described by the general structure I include the structures where X is a moiety derived from substituted pyridine, such as compounds having the general structure II:

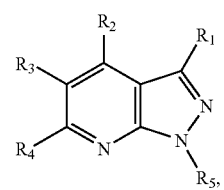

II

In the general structure II, $R_1$ is selected from a group consisting of a substituted alkenyl and a substituted alkynyl, wherein the substitutent(s) in each of the substituted alkenyl and the substituted alkynyl is (are) selected from the group consisting of an aryl, a substituted aryl, a heteroaryl, and a substituted heteroaryl; $R_2$ is selected from a group consisting of a halogen, an unsubstituted aryl, a substituted aryl, an unsubstituted heteroaryl, a substituted heteroaryl, an unsubstituted alkyl, a substituted alkyl, and $(CH_2)_nOR_6$; $R_3$ is selected from a group consisting of H, an unsubstituted aryl, a substituted aryl, an unsubstituted heteroaryl, a substituted heteroaryl, an unsubstituted alkyl, and a substituted alkyl; $R_4$ is selected from a group consisting of OH and OR$_7$; each of R$_5$, R$_6$ and R$_7$ is independently selected from a group consisting of an unsubstituted alkyl and a substituted alkyl; and n is an integer having the value of 1, 2, or 3.

Examples of some other sub-genera that are within the purview of the present invention and are described by the general structure I include the structures, where X is a moiety derived from substituted pyrimidine, such as compounds having the general IIIA or IIIB:

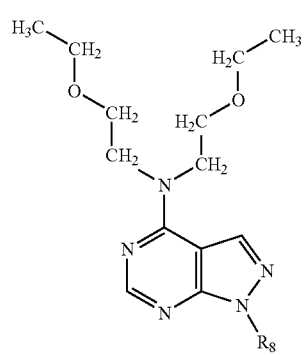

IIIA

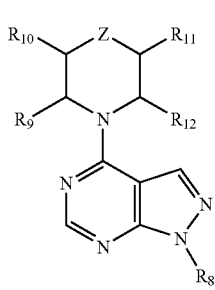

IIIB

In the general structures IIIA and IIIB, R$_8$ is selected from a group consisting of an unsubstituted aryl and a substituted aryl; each of R$_9$, R$_{10}$, R$_{11}$, and R$_{12}$ is selected from a group consisting of an unsubstituted alkyl, a substituted alkyl, an acyl, an unsubstituted aryl, a substituted aryl, and a halogen; and Z is selected from a group consisting of C, O, and N.

Non-limiting examples of some specific compounds that are within the purview of the present invention include the compounds 1-37:

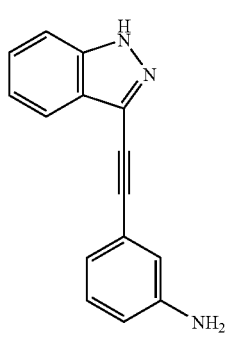

1

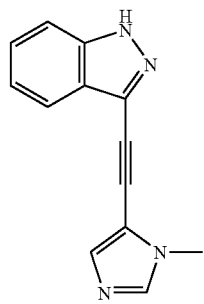

2

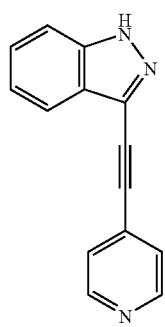

3

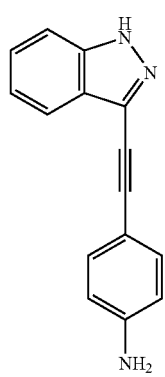

4

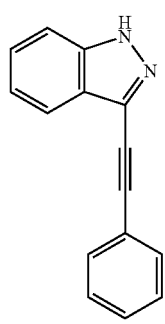

5

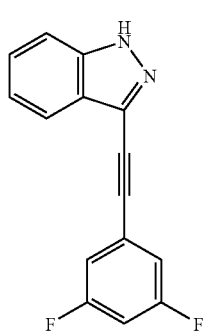

6

7
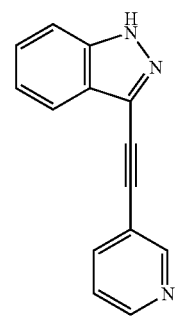
8
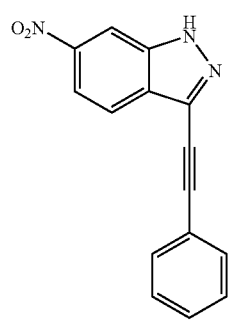
9
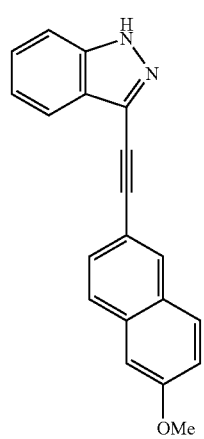
10
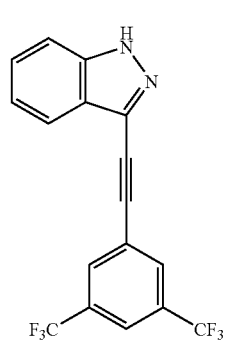
11
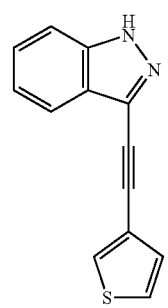
12
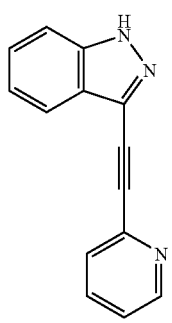
13
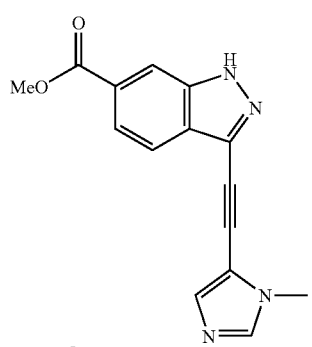
14
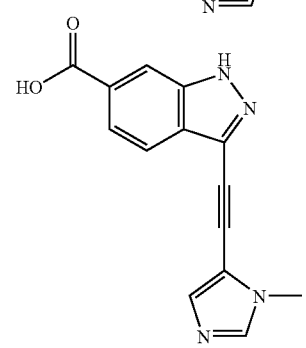
15
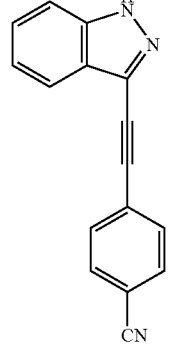

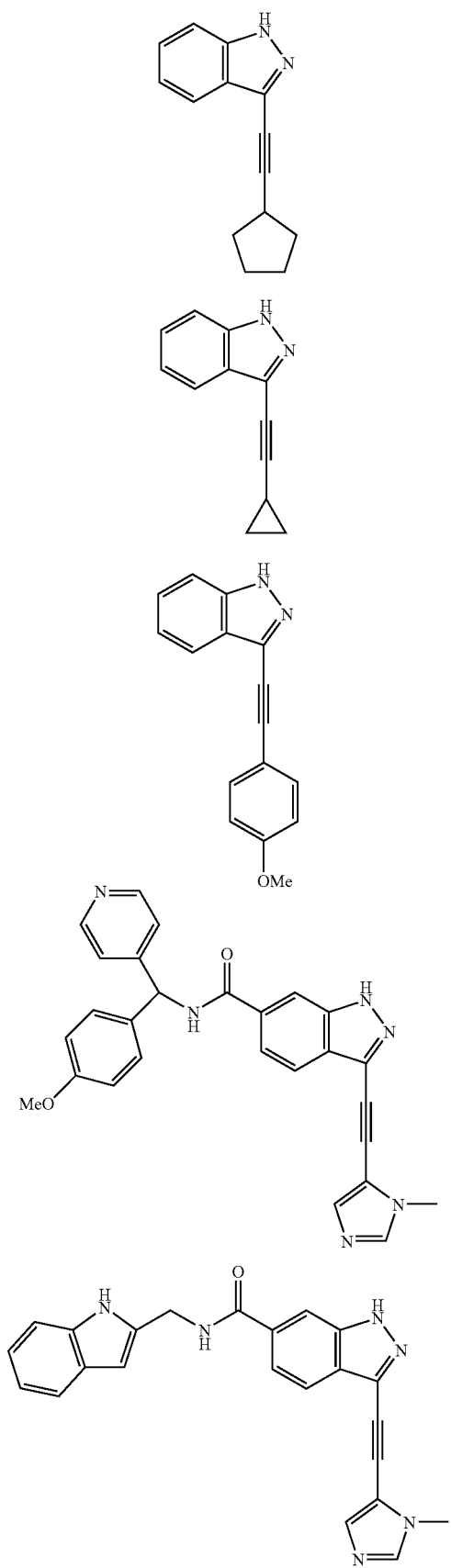
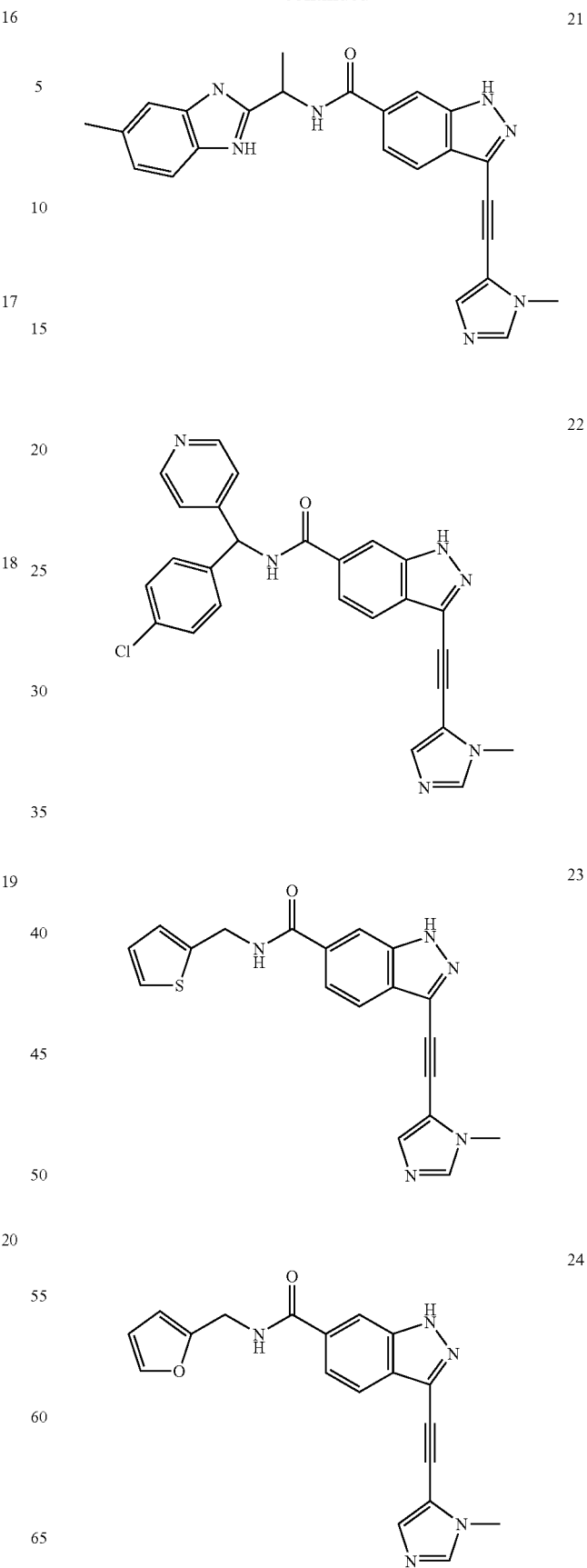

13
-continued
25
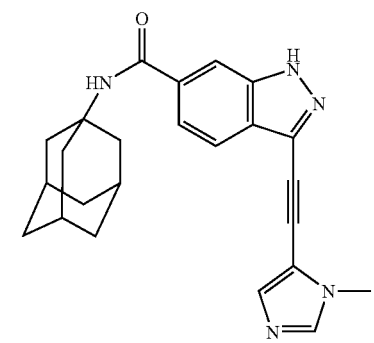
26
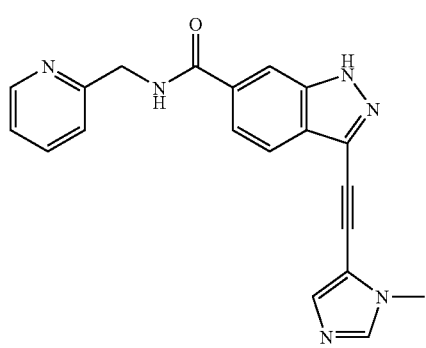
27
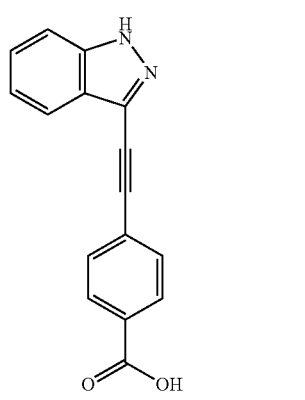
28
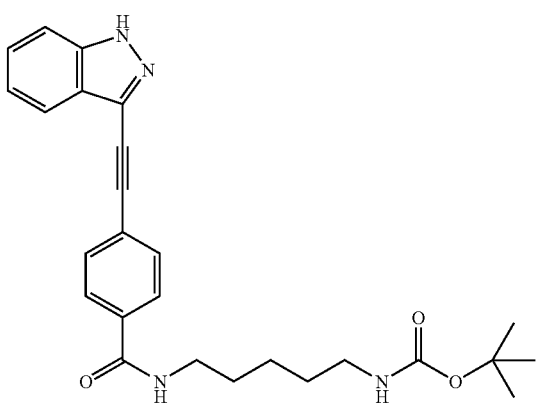
14
-continued
29
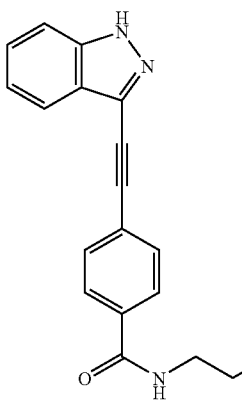
30
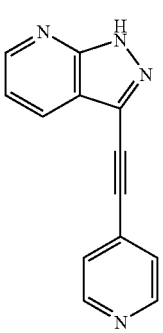
31
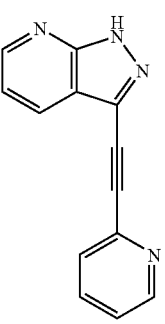
32
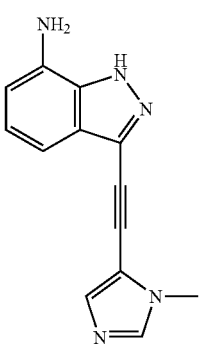

The compounds of the present invention are capable of inhibiting kinase, for example, by selectively targeting at the kinases PI3 K-AKT-mTOR signal transduction pathway, for the treatment of various disorders, diseases, and pathologies, such as cancer. Accordingly, the compounds having the structure I, including sub-genera II, IIIA and IIIB, or pharmaceutically acceptable salts thereof can be used for preparing pharmaceutical compositions, e.g., by combining these compounds and pharmaceutically acceptable carriers. The pharmaceutical compositions can then be used in pharmacologically effective doses for the treatment of various disorders, diseases, and pathologies, such as cancer.

Various synthetic schemes can be designed for manufacturing the products having the structure I, including the sub-genera II, IIIA and IIIB. Two such schemes, as applicable to compounds of the sub-genera II and IIIA are shown below as reaction schemes A and B, respectively.

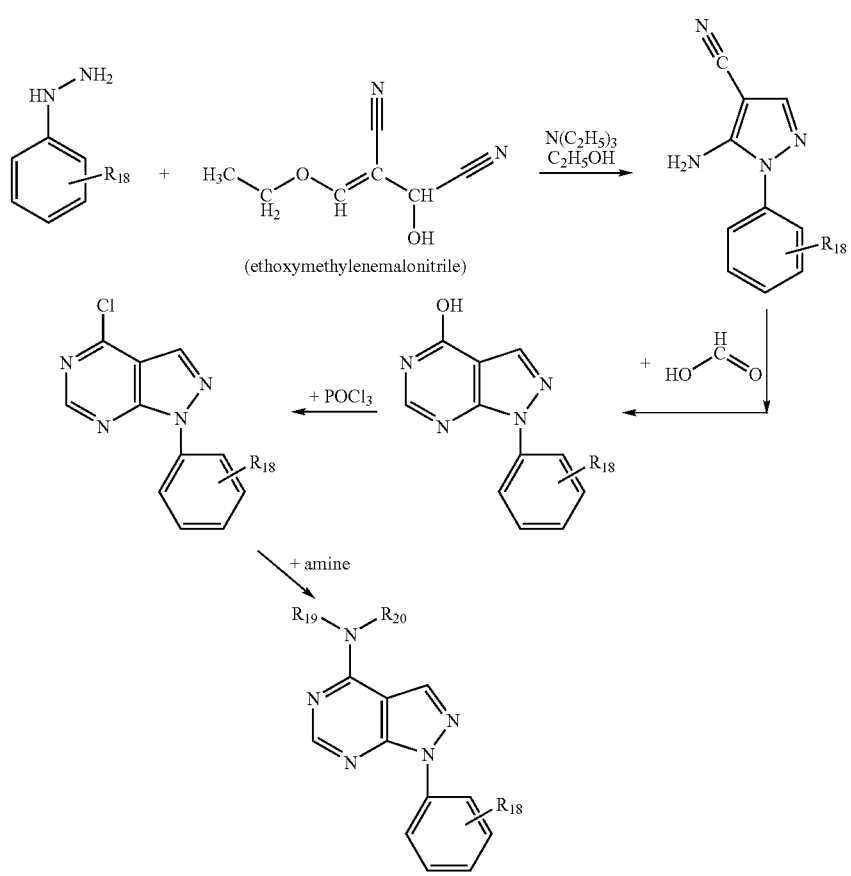

Pharmaceutically acceptable salts of the compounds of the present invention may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The above-described compounds I, including the sub-genera II, IIIA and IIIB can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds I, including the sub-genera II, IIIA and IIIB can be determined by comparing their in vitro activity, and in vivo activity in animal models. Methods for the extrapolation of effective dosages in mice, and other animals, to humans are known to those having ordinary skill in the art who can, for example, be guided by the procedures described in U.S. Pat. No. 4,938,949.

Generally, the concentration of the compound(s) I, including the sub-genera II, IIIA and IIIB in a liquid composition, such as a lotion, can be between about 0.1 and 25 mass %, such as between about 0.5 and 10 mass %. The concentration in a semi-solid or solid composition such as a gel or a powder can be between about 0.1 and 25 mass %, such as between about 0.5 and 2.5 mass %.

The amount of the compound(s) I, including the sub-genera II, IIIA and IIIB, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose can be in the range of between about 0.5 and 100 mg/kg, e.g., between about 10 and 75 mg/kg of body weight per day, such as between about 15 and 60 mg/kg/day. The compound(s) I, including the sub-genera II, IIIA and IIIB can be conveniently administered in unit dosage form; for example, containing 5 to 1000 mg, such as 10 to 750 mg, for example, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Figure 2:
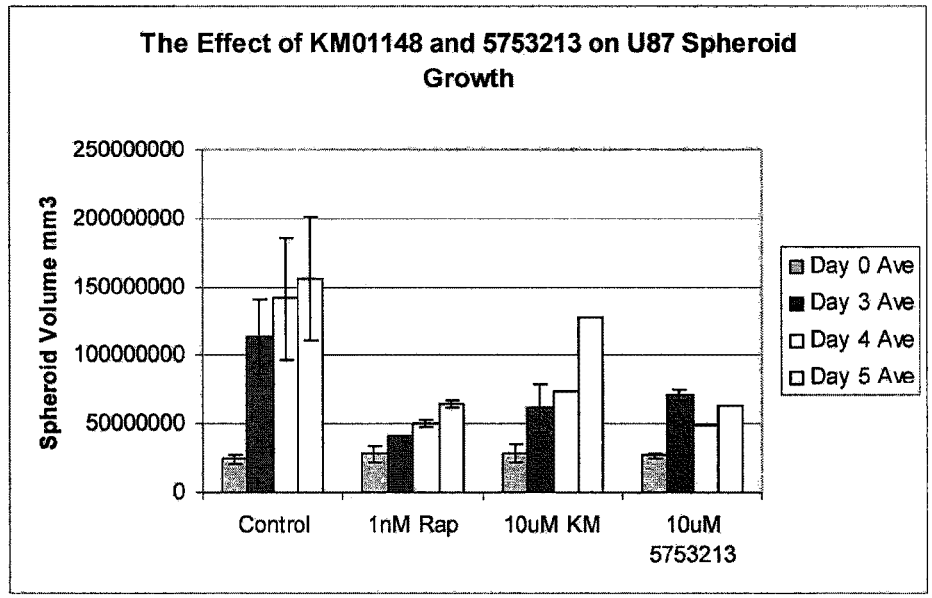
FIG. 2 shows the data on inhibition of U87 spheroid cell growth by some compounds of the present invention, according to one embodiment of the present invention.
Figure 3:
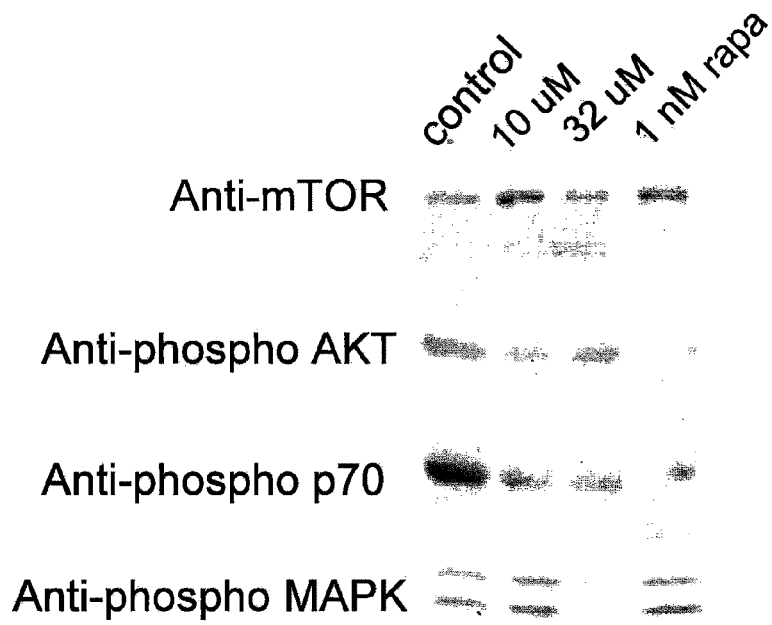
FIG. 3 shows the data on inhibition of target kinase activities in U87 spheroid cell by some compounds of the present invention, according to one embodiment of the present invention.
Figure 4:
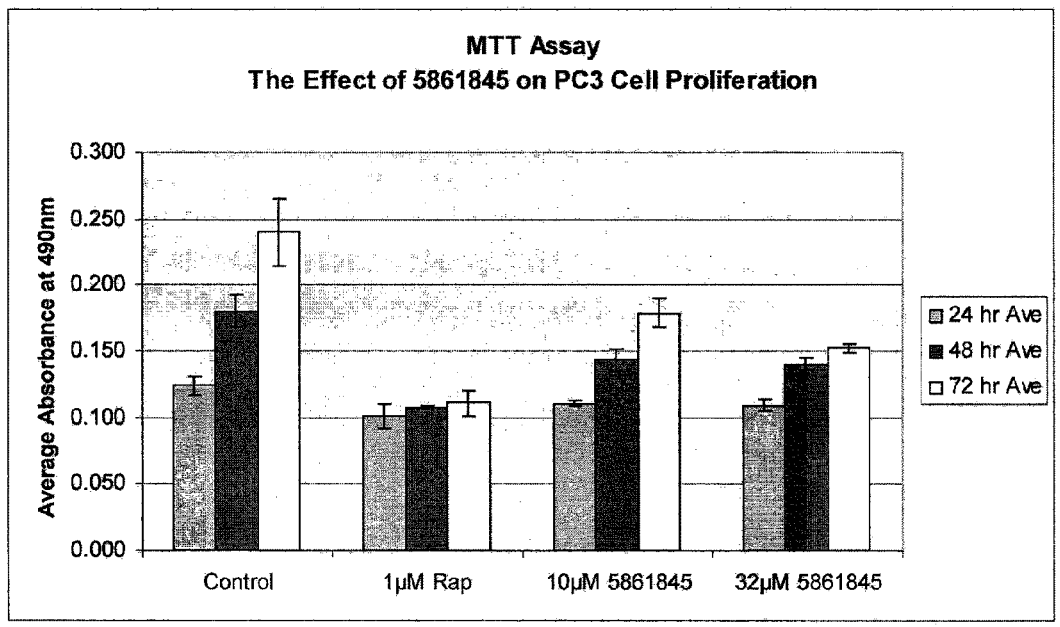
FIG. 4 shows the data on inhibition of PC3 cell proliferation by some compounds of the present invention, according to another embodiment of the present invention.

FIGS. 1-7 further exemplify embodiments of the present invention, which are are intended to further illustrate but not limit the invention. FIG. 1 illustrates inhibition of PC3 cell proliferation by pyrazolopyridines (the above shown compounds of the sub-genera II). FIG. 4 illustrates inhibition of PC3 cell proliferation by amininopyrimidines (the above shown compounds of the sub-genera IIIA). As can be seen from FIGS. 1 and 4, a substantial degree of inhibition has been achieved.

Figure 5:
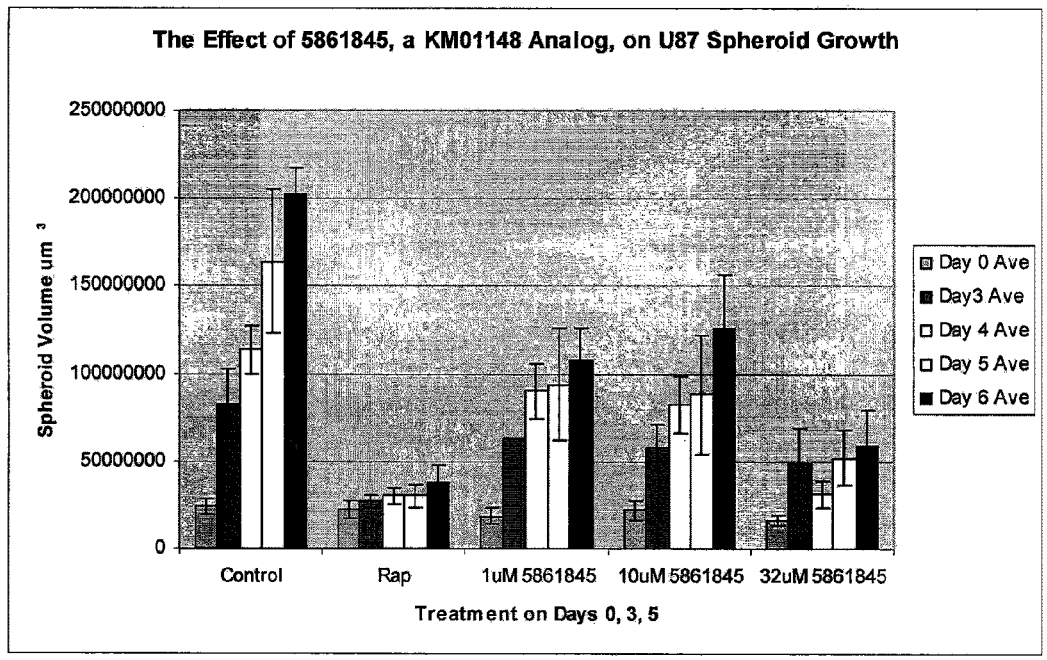
FIG. 5 shows the data on inhibition of U87 spheroid cell growth by some compounds of the present invention, according to another embodiment of the present invention.

FIG. 2 illustrates inhibition of U87 spheroid cell growth by pyrazolopyridines (the above shown compounds of the sub-genera II). FIG. 5 illustrates inhibition of U87 spheroid cell growth by amininopyrimidines (the above shown compounds of the sub-genera IIIA).

Figure 6:
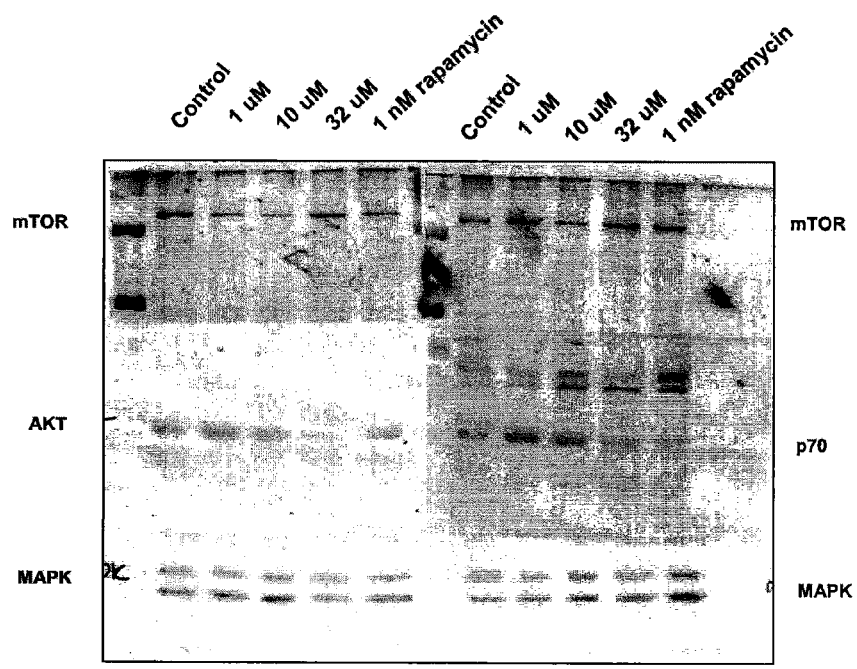
FIG. 6 shows the data on inhibition of target kinase activities in U87 spheroid cell by some compounds of the present invention, according to another embodiment of the present invention.
Figure 7:
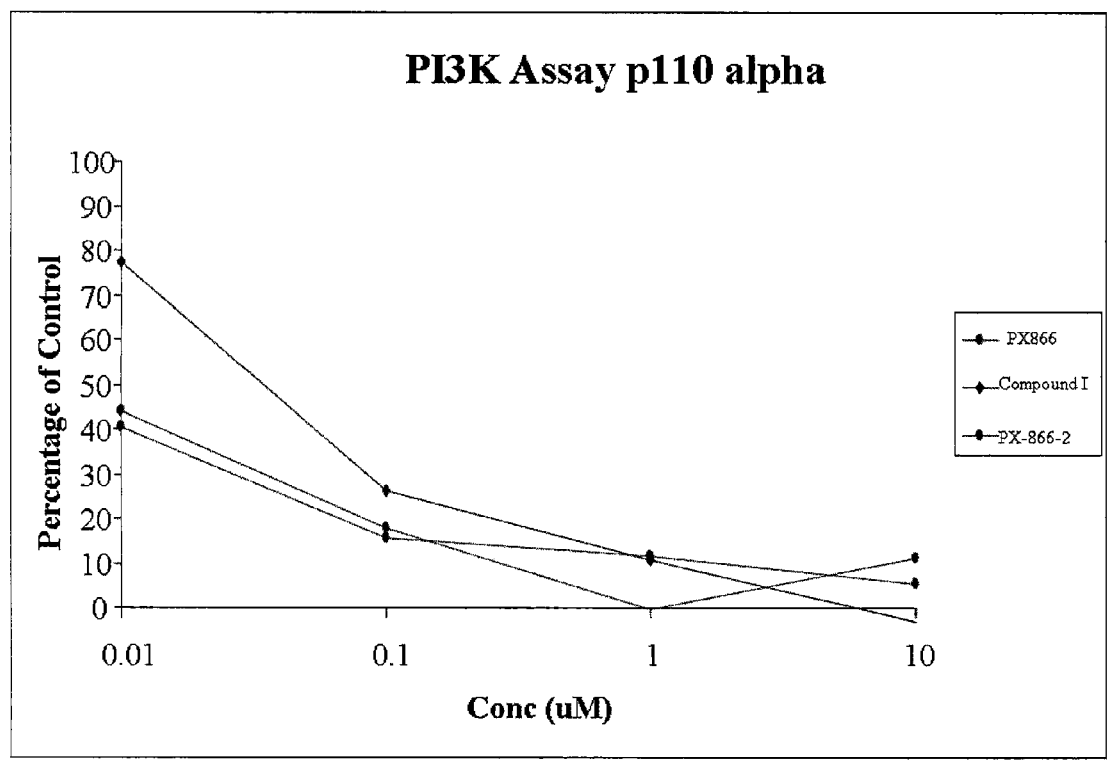
FIG. 7 shows the PI3K assay data, including compound 1 of the invention.

Finally, FIG. 3 shows the data on inhibition of target kinase activities in U87 spheroid cell by pyrazolopyridines (the above shown compounds of the sub-genera II), while FIG. 6 shows the same for amininopyrimidines (the above shown compounds of the sub-genera IIIA). These figures provide additional information as to the effectiveness of inhibition using compounds of the present invention.

Table 1 below provides shows the data on inhibition of PI3K and mTOR kinases by some compounds of the invention.

TABLE 1
Assay results in Inhibition PI3K and mTOR by Compounds of the Invention
| Structure | PI3 K (% at 25 μM, or IC$_{50}$), P110α, μM | mTOR (Inhibition % at 50 μM, or IC$_{50}$) |
|---|---|---|
| 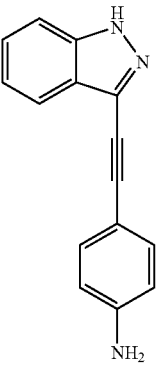 | 0.083 | 9% |
| 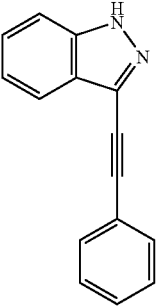 |  | 6% |
| 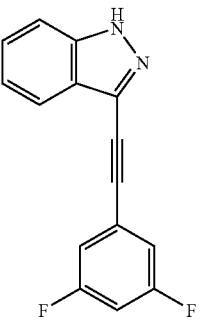 |  | 6% |
| 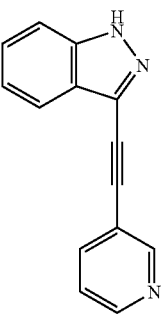 | 0.075 | 34% |

TABLE 1-continued

Assay results in Inhibition PI3K and mTOR by Compounds of the Invention

| Structure | PI3 K (% at 25 µM, or IC$_{50}$), P110α, µM | mTOR (Inhibition % at 50 µM, or IC$_{50}$) |
|---|---|---|
| (indazole-C≡C-pyridin-4-yl) | 0.299 | 30% (IC$_{50}$ > 100 uM) |
| (indazole-C≡C-1-methylimidazol-5-yl) | 0.062 | 46% (IC$_{50}$ > 100 uM) |
| (6-nitro-indazole-C≡C-phenyl) | | −1% |
| (indazole-C≡C-6-methoxynaphthalen-2-yl) | | 5% |

TABLE 1-continued

Assay results in Inhibition PI3K and mTOR by Compounds of the Invention

| Structure | PI3 K (% at 25 µM, or IC$_{50}$), P110α, µM | mTOR (Inhibition % at 50 µM, or IC$_{50}$) |
|---|---|---|
| (1H-indazol-3-yl)ethynyl-3,5-bis(trifluoromethyl)benzene | | −3% |
| (1H-indazol-3-yl)ethynyl-thiophene | | 7% |
| (1H-indazol-3-yl)ethynyl-pyridine | | 13% |
| methyl 3-((1-methyl-1H-imidazol-5-yl)ethynyl)-1H-indazole-6-carboxylate | | 4% |

TABLE 1-continued

Assay results in Inhibition PI3K and mTOR by Compounds of the Invention

| Structure | PI3 K (% at 25 µM, or IC$_{50}$), P110α, µM | mTOR (Inhibition % at 50 µM, or IC$_{50}$) |
|---|---|---|
| | | 24% |
| | | 1% |
| 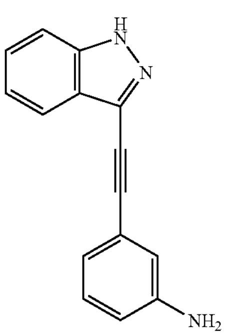 | 0.058 | 9% |
| | | 3% |

TABLE 1-continued
Assay results in Inhibition PI3K and mTOR by Compounds of the Invention
| Structure | PI3 K (% at 25 μM, or IC$_{50}$), P110α, μM | mTOR (Inhibition % at 50 μM, or IC$_{50}$) |
|---|---|---|
| 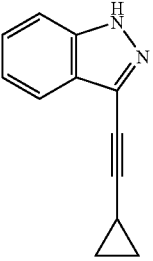 | | 2% |
| 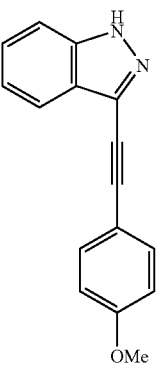 | | 5% |
| 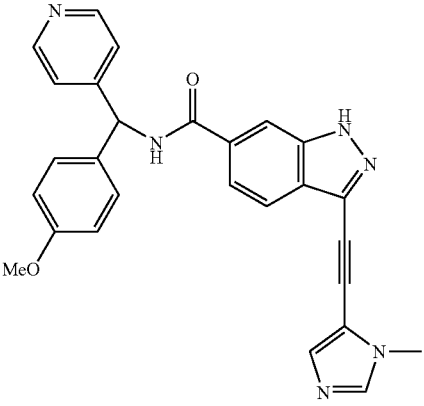 | 0.082 | |
| 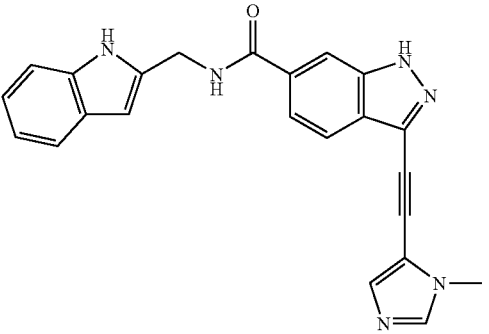 | | 3% |

TABLE 1-continued

Assay results in Inhibition PI3K and mTOR by Compounds of the Invention

| Structure | PI3 K (% at 25 μM, or IC$_{50}$), P110α, μM | mTOR (Inhibition % at 50 μM, or IC$_{50}$) |
|---|---|---|
| | | −7% |
| | | −27% |
| | | −14% |
| | | −5% |

TABLE 1-continued

Assay results in Inhibition PI3K and mTOR by Compounds of the Invention

| Structure | PI3 K (% at 25 μM, or IC$_{50}$), P110α, μM | mTOR (Inhibition % at 50 μM, or IC$_{50}$) |
|---|---|---|
| | | −11% |
| | | −17% |
| | | 31 μM |
| | | −6% |

TABLE 1-continued

Assay results in Inhibition PI3K and mTOR by Compounds of the Invention

| Structure | PI3 K (% at 25 μM, or IC$_{50}$), P110α, μM | mTOR (Inhibition % at 50 μM, or IC$_{50}$) |
|---|---|---|
| | | 3% |
| | | 15% |
| | | 7% |

Although the invention has been described with reference to the above example, it will be understood that modifications and variations are encompassed within the spirit and scope of the invention. Accordingly, the invention is limited only by the following claims.

What is claimed is:

1. A compound selected from compounds 1, 3, 4, and 7:

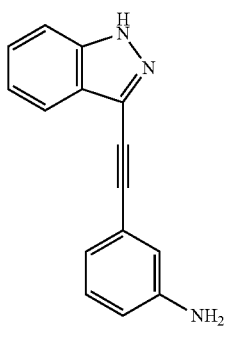

1

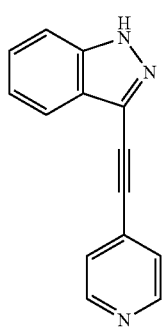

3

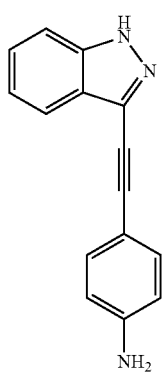

4

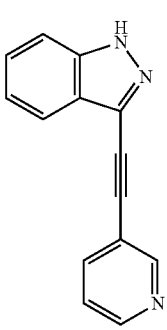

7 or a pharmaceutically acceptable salt thereof.

2. The compound of claim 1, wherein the compound is compound 1 or compound 3:

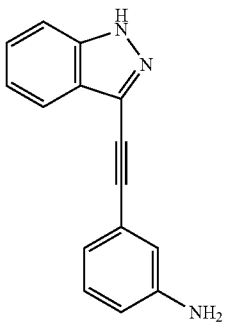

1

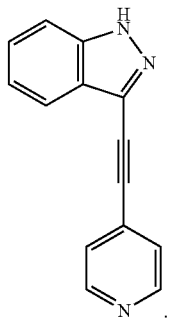

3

3. The compound of claim 1, wherein the compound is compound 1:

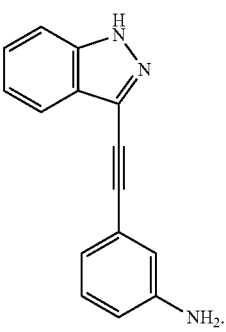

1

4. The compound of claim 1, wherein the compound is compound 3:

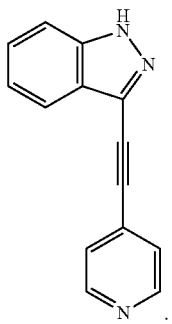

3

5. A pharmaceutical composition comprising compound 1, 3, 4, or 7 of claim 1, and a pharmaceutically acceptable carrier.

6. A kit comprising a packaging material and a pharmaceutical composition according to claim 5 contained within the packaging material, wherein the packaging material comprises a label which indicates that the composition can be used for treating a disorder, disease, or pathology in a subject in need thereof.

* * * * *